United States Patent
Yang et al.

(10) Patent No.: US 12,426,612 B2
(45) Date of Patent: Sep. 30, 2025

(54) ***BIDENS PILOSA* AND ITS PHYTOCHEMICALS FOR USE IN PREVENTION AND TREATMENT OF DIARRHEA**

(71) Applicant: Academia Sinica, Taipei (TW)

(72) Inventors: Wen-Chin Yang, Taichung County (TW); Yu-Chuan Liang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 834 days.

(21) Appl. No.: 17/598,284

(22) PCT Filed: Mar. 22, 2020

(86) PCT No.: PCT/US2020/024106
§ 371 (c)(1),
(2) Date: Sep. 26, 2021

(87) PCT Pub. No.: WO2020/198093
PCT Pub. Date: Oct. 4, 2020

(65) Prior Publication Data
US 2022/0174986 A1    Jun. 9, 2022

Related U.S. Application Data

(60) Provisional application No. 62/825,768, filed on Mar. 28, 2019.

(51) Int. Cl.
*A23K 10/30* (2016.01)
*A23K 50/30* (2016.01)
*A61K 36/28* (2006.01)

(52) U.S. Cl.
CPC .............. *A23K 10/30* (2016.05); *A23K 50/30* (2016.05); *A61K 36/28* (2013.01)

(58) Field of Classification Search
None
See application file for complete search history.

(56) References Cited

U.S. PATENT DOCUMENTS

| 10,568,897 | B2 * | 2/2020 | Yang | A61P 33/02 |
| 10,632,165 | B2 * | 4/2020 | Yang | A23K 20/105 |
| 2014/0308278 | A1 * | 10/2014 | Hansen | A61K 49/221 |
| | | | | 530/389.7 |
| 2014/0308378 | A1 | 10/2014 | Yang et al. | |
| 2018/0333447 | A1 | 11/2018 | Yang et al. | |

FOREIGN PATENT DOCUMENTS

| CN | 105106269 A | * | 12/2015 | |
| EP | 1407679 A1 | * | 4/2004 | A23K 10/30 |

OTHER PUBLICATIONS

Burrough (Brachyspira-associated colitis in swine, May 7, 2012) (Year: 2012).*
Thompson Show Feed, acceessed online Mar. 20, 2025 (Year: 2025).*
International Search Report for PCT/US2020/024106, dated Jul. 6, 2020.
Written Opinion of International Search Authority for PCT/US2020/024106, dated Jul. 6, 2020.

* cited by examiner

*Primary Examiner* — Melissa S Mercier
(74) *Attorney, Agent, or Firm* — Hsiu-Ming Saunders; INTELLECTUAL PROPERTY CONNECTIONS, INC.

(57) ABSTRACT

A composition comprising *Bidens pilosa* or an active compound isolated from the *Bidens pilosa* for use in treating, inhibiting and/or decreasing the presence of pathogenic gut microbiota in an animal in need thereof is disclosed. The pathogenic gut microbiota are at least one selected from the group consisting of *Brachyspira*, porcine epidemic diarrhea virus (PEDV), transmissible gastroenteritis coronavirus (TGEV) and Rotavirus (RV). The composition is also for use in treating, inhibiting and/or decreasing occurrence of swine diarrhea, swine dysentery, swine viral infection and increasing the percentage of swine carcass and bone weight. In one embodiment, the composition is for use in treating, inhibiting and/or decreasing occurrence of swine dysentery associated with *Brachyspira*.

20 Claims, 5 Drawing Sheets

Specification includes a Sequence Listing.

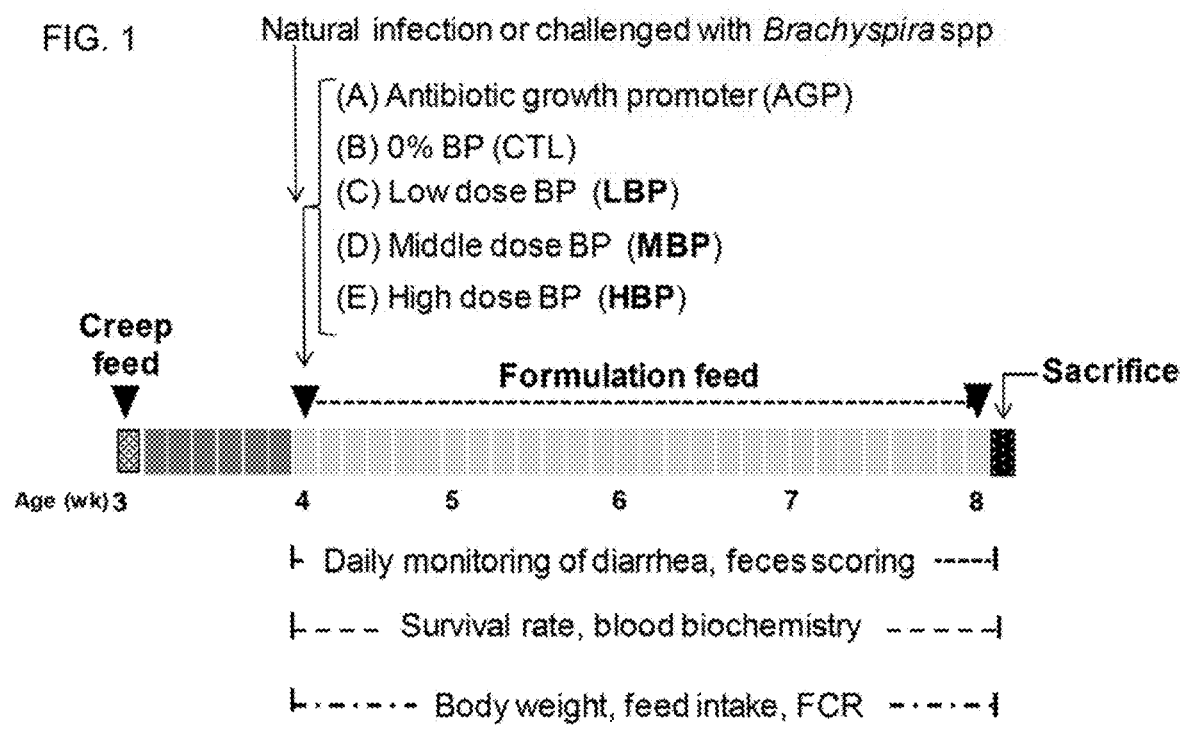
FIG. 1
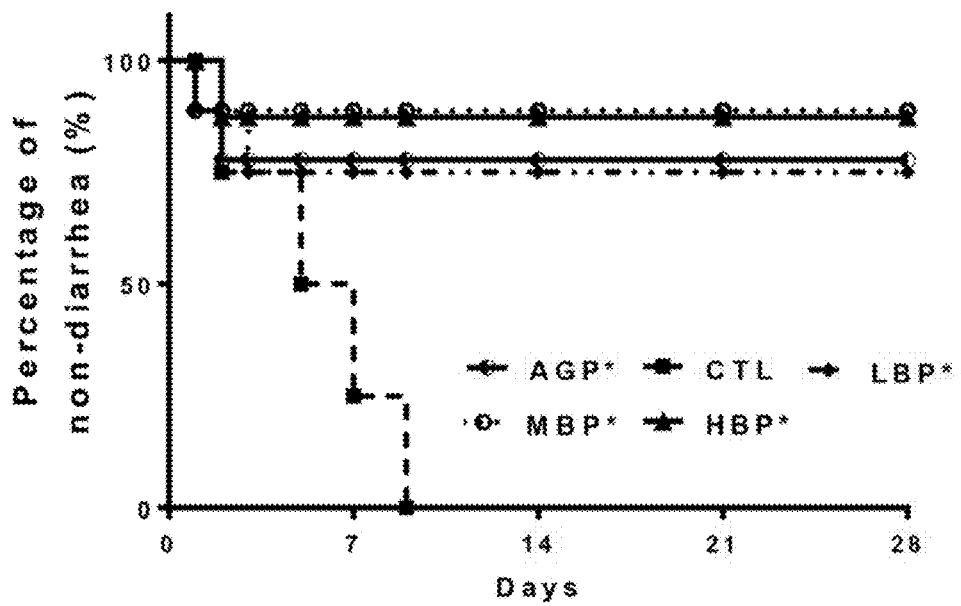
FIG. 2A
FIG. 2B
| Comparison | P value |
| --- | --- |
| CTL (0% BP) vs AGP | 0.0408 |
| CTL (0% BP) vs LBP | 0.0433 |
| CTL (0% BP) vs MBP | 0.0145 |
| CTL (0% BP) vs HBP | 0.0115 |

BIDENS PILOSA AND ITS PHYTOCHEMICALS FOR USE IN PREVENTION AND TREATMENT OF DIARRHEA

REFERENCE TO RELATED APPLICATION

This application is a national stage application (under 35 U.S.C. 371) of PCT/US2020/024106 filed on 22 Mar. 2020, which claims priority to U.S. provisional application 62/825,768 filed on 28 Mar. 2019, all of which are herein incorporated by reference in their entireties.

FIELD OF THE INVENTION

The present invention relates generally to *Bidens pilosa* for use in the prevention, alleviation and treatment of diarrhea, and more specifically to *Bidens pilosa* and its phytochemicals for use in preventing alleviating and treating swine diarrhea.

BACKGROUND OF THE INVENTION

Diarrhea and dysentery are the most important problems in the swine industry. It can occur from weaning through the last day of finisher. It can become a chronic condition that continues for weeks. Antimicrobial growth promoters (AGP) as feed additives have proved to be effective in decreasing porcine diarrhea and enhancing growth performance in the swine industry. However, AGP has been known to induce antibiotic resistance in pathogens. Therefore, APG for animals has been banned in the European Union since 2006.

Plants have been an extraordinary source of medicines for humans and animals since antiquity. An herbal approach may reduce or replace the abuse or misuse of AGP in swine and help meat production.

SUMMARY OF THE INVENTION

In one aspect, the invention relates to use of a composition comprising *Bidens pilosa* or an active compound isolated from the *Bidens pilosa* in the manufacture of a medicament for treating, inhibiting and/or decreasing the presence of pathogenic gut microbiota in an animal in need thereof, wherein the pathogenic gut microbiota are at least one selected from the group consisting of *Brachyspira* spp., porcine epidemic diarrhea virus (PEDV), transmissible gastroenteritis coronavirus (TGEV) and Rotavirus (RV).

The composition of the invention is also for use in increasing the percentage of swine carcass and bone weight.

In another aspect, the invention relates to use of a composition comprising *Bidens pilosa* or an active compound isolated from the *Bidens pilosa* in the manufacture of a medicament for treating, inhibiting and/or decreasing occurrence of swine diarrhea, swine dysentery, swine viral infection and increasing the percentage of swine carcass and bone weight.

Further in another aspect, the invention relates to use of a composition comprising *Bidens pilosa* or an active compound isolated from the *Bidens pilosa* in the manufacture of a medicament for treating and/or decreasing occurrence of swine dysentery associated with *Brachyspira* and increasing the percentage of swine carcass and bone weight.

In one embodiment of the invention, the swine diarrhea, swine dysentery and swine viral infection are associated with at least one of pathogenic gut microbiota selected from the group consisting of *Brachyspira*, porcine epidemic diarrhea virus (PEDV), transmissible gastroenteritis coronavirus (TGEV) and Rotavirus (RV).

In one embodiment, the pathogenic gut microbiota may be selected from *Brachyspira* spp. The pathogenic gut microbiota may be *Brachyspira hyodysenteriae*. The animal in need thereof may be a weaning pig or a grown-up pig.

In another embodiment, the active compound isolated from the *Bidens pilosa* is a polyacetylenic compound of formula (I):

$$R_1\text{-}(C\equiv C)_m\text{-}(\underset{H}{C}=\underset{H}{C})_n\text{-}(\phantom{x})_o\text{-}\underset{\underset{OR_2}{|}}{C}\text{-}(\phantom{x})_p\text{-}OR_3,$$ (I)

wherein
R$_1$ is H or CH$_3$;
R$_2$ is monosaccharide;
R$_3$ is H or COCH$_2$COOH;
m=3 or 4;
n=0 or 1;
o=1 or 2; and
p=1 or 2.

In another embodiment, the active compound isolated from the *Bidens pilosa* is at least one selected from the group consisting of

A: R = COCH$_2$COOH
A': R = H

B: R = COCH$_2$COOH
B': R = H

C: R = COCH$_2$COOH
C': R = H

The *Bidens pilosa* may be in a powder form. The composition may be in the form of food, an animal feed material or a medicine.

In another embodiment, the composition is in a dosage form selected from the group consisting of oral, capsule, suppository and parenteral.

In another embodiment, the *Bidens pilosa* or the active compound isolated from the *Bidens pilosa* is at a dosage of no less than 1 μg/kg body weight of the animal in need thereof.

In another embodiment, the composition comprises an animal feed and the *Bidens pilosa* ranging from 0.0005% to 15% (w/w).

In another embodiment, the composition comprises an animal feed and the *Bidens pilosa* ranging from 0.05% to 15% (w/w). The composition may comprise an animal feed and the *Bidens pilosa* ranging from 0.1% to 15% (w/w), 1% to 15% (w/w) or 1% to 10% (w/w).

In another embodiment, the active compound isolated from the *Bidens pilosa* is cytopiloyne.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1 shows a dosing schedule. Five groups of 4-week-treated weaning piglets fed with antibiotic growth promoter (AGP), standard diet (0% BP) and standard diet containing *B. pilosa* powder (LBP, MBP and 1-BP) for 4 weeks. LBP, MBP and HPB refer to a diet containing 1, 2, 5% *B. pilosa* powder, respectively.

FIG. 2 shows the effect of *B. pilosa* on diarrhea in weaning piglets. Piglets developed diarrhea on natural infection. Occurrence of diarrhea was monitored every day for 28 days. The piglets' number was 10 for each group. The p values were estimated by Kaplan-Meier log-rank test to determine the difference in outcomes between control (0% BP) and each treatment groups and p<0.05 (*) are shown (A). Table showing the p-values for pairwise comparisons of non-diarrhea curves (B).

DETAILED DESCRIPTION OF THE INVENTION

Definitions

Figure 3:
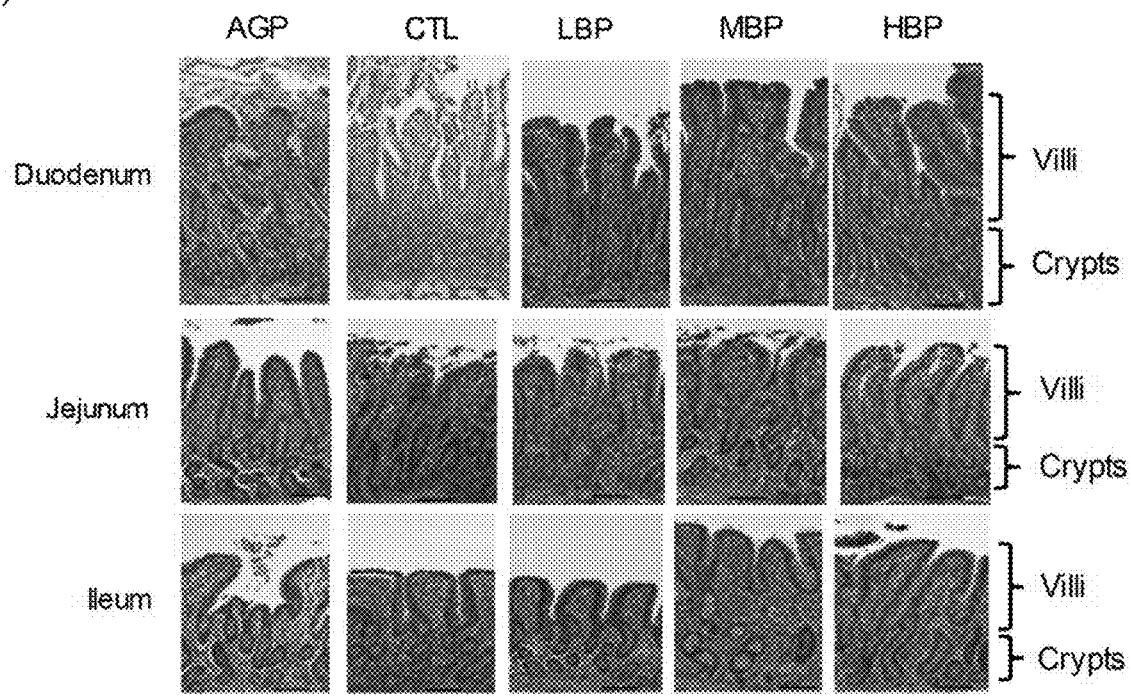
FIG. 3 shows the effect of *B. pilosa* on gut pathology in swine. (A) Hematoxylin and eosin (H&E) staining of the duodenum ($1^{st}$ row), jejunum ($2^{nd}$ row), and ileum ($3^{rd}$ row) of the swine. (B) Vilium-to-crypt length ratio of the duodenum (left panel), jejunum (middle panel) and ileum (right panel) of the swine. ANOVA was used to compare the difference between control (0% BP) and each treatment groups and p<0.05 (*) are shown.
Figure 3:
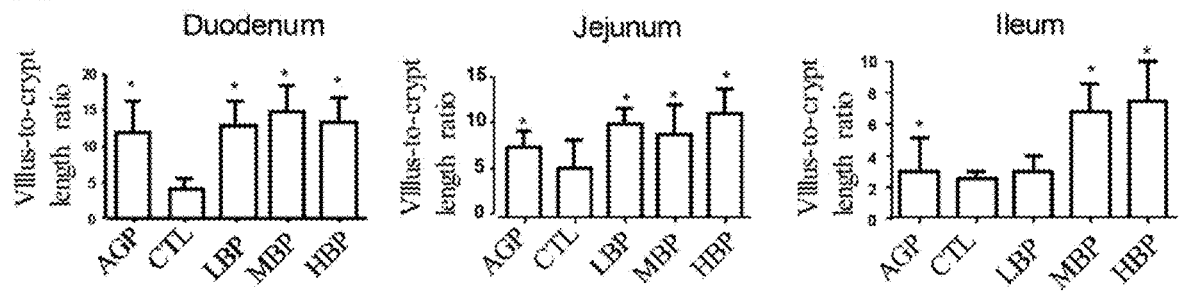

An animal feed refers to food given to domestic livestock, and pet (companion animal) food.

The term "pure compound" used herein refers to a compound that has a purity of at least 80% (e.g., 95% or 99%).

The term "treating" or "treatment" refers to use of an effective agent to a subject in need thereof with the purpose to cure, alleviate, relieve, remedy, ameliorate, reduce, or to prevent the disease, the symptoms of it, or the predispositions towards it.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

$$HED = \text{animal dose in mg/kg} \times (\text{animal weight in kg/human weight in kg})^{0.33}.$$

The invention relates to a phytogenic to replace antimicrobial growth promoters (AGP) in swine feed additives for decreasing porcine diarrhea, improve swine health and enhancing growth performance.

*B. pilosa* powder was prepared first. Animal diets were formulated by mixing with different percentages of the *B. pilosa* powder.

*Bidens pilosa* preparation. The preparation can be obtained by stirring pulverized *Bidens pilosa* plants in water at an elevated temperature (e.g., at 50° C. or 100° C.) to form a suspension, and collecting a supernatant of the suspension. The supernatant can be further extracted with an alcohol (e.g., n-butanol) to provide an enriched preparation. The *Bidens pilosa* preparation (extract) contains one or more of the polyacetylenic compounds. For example, it contains cytopiloyne:

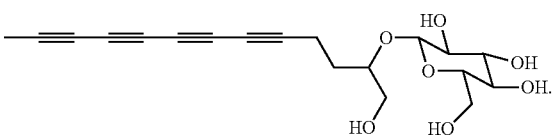

The polyacetylenic compounds described above include the compounds themselves, as well as their salts, prodrugs, and solvates, if applicable. Such salts, for example, can be formed by interaction between a negatively charged substituent (e.g., carboxylate) on a polyacetylenic compound and a cation. Suitable cations include, but are not limited to, sodium ion, potassium ion, magnesium ion, calcium ion, and an ammonium cation (e.g., tetramethylammonium ion). Likewise, a positively charged substituent (e.g., amino) on a polyacetylenic compound can form a salt with a negatively charged counterion. Suitable counterions include, but are not limited to, chloride, bromide, iodide, sulfate, nitrate, phosphate, or acetate. Examples of prodrugs include esters and other pharmaceutically acceptable derivatives, which, upon administration to a subject, are capable of providing above compounds described above. A solvate refers to a complex formed between a polyacetylenic compound and a pharmaceutically acceptable solvent. Examples of pharmaceutically acceptable solvents include water, ethanol, isopropanol, n-butanol, ethyl acetate, and acetic acid.

The polyacetylenic compounds may contain one or more asymmetric centers or a non-aromatic double bond. Thus, they can occur as racemates and racemic mixtures, single enantiomers, individual diastereomers, diastereomeric mixtures, and cis- or trans-isomeric forms. All such isomeric forms are contemplated.

Polyacetylenic Compounds

Polyacetylenic compounds (e.g., cytopiloyne) can be isolated from *Bidens pilosa*. Whole *Bidens pilosa* plants are first pulverized and then stirred in heated water. After removal of insoluble materials (e.g., by filtration, decantation, or centrifugation), the resultant supernatant is subjected to liquid chromatography (e.g., high-pressure liquid chromatography) or other suitable methods to afford pure polyacetylenic compounds. The pure compounds thus obtained can be further derivatized to provide a number of other polyacetylenic compounds of this invention (U.S. Pat. No. 7,763,285, and Kusano et al (JP 2004083463), all of which are incorporated herein by reference in their entireties).

The polyacetylenic compounds described above can also be prepared by conventional methods. Below are three reaction schemes illustrating synthetic routes to a polyacetylenic compound of this invention.

Scheme 1

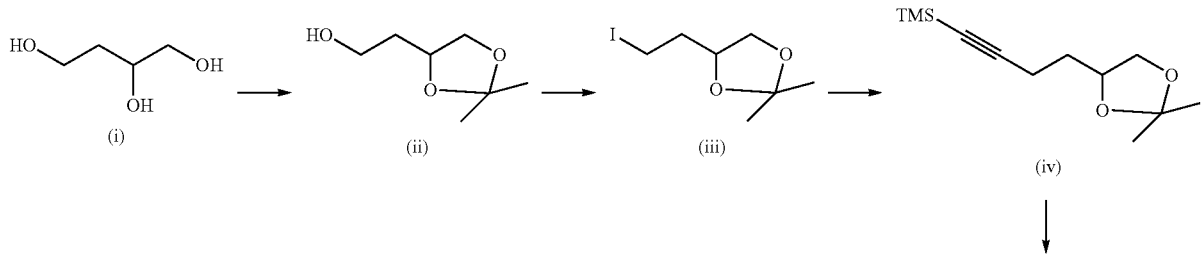

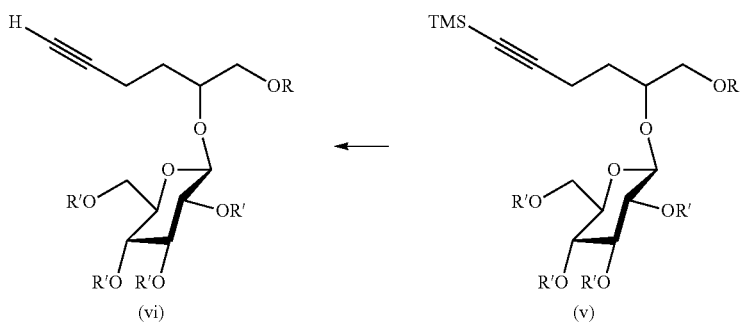

Butane-1,2,4-triol (i) is reacted with acetone to form a protected 1,2,4-triol compound (ii), which can be readily transformed to an iodo derivative (iii). Compound (iii) is then reacted with ethynyltrimethylsilane, under a basic condition (e.g., n-BuLi), to give (4-(2,2-dimethyl-1,3-dioxolan-4-yl)but-1-ynyl)trimethylsilane (iv). Compound (iv) is subsequently treated with an acid (e.g., acetic acid), followed by a coupling reaction with 2-bromoglucopyranose to afford an adduct (v). Compound (v) can be further treated with potassium fluoride to afford 2-phenyl-4H-chromen-4-one (vi).

Scheme 2

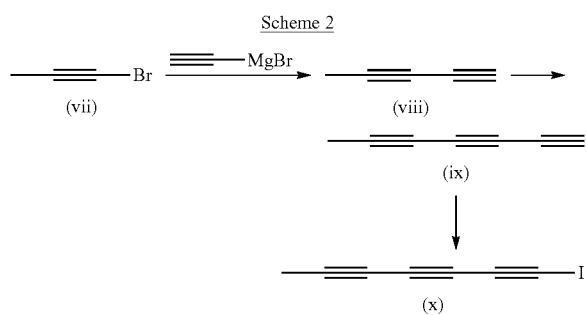

1-Bromoprop-1-yne (vii) is reacted with ethynylmagnesium bromide to afford penta-1,3-diyne (viii), which is further converted to hepta-1,3,5-triyne (ix). Compound (ix) can be readily transformed to 1-iodohepta-1,3,5-triyne (x) under a basic condition (e.g., n-BuLi), followed by addition of an iodo compound (e.g., 12).

Scheme 3

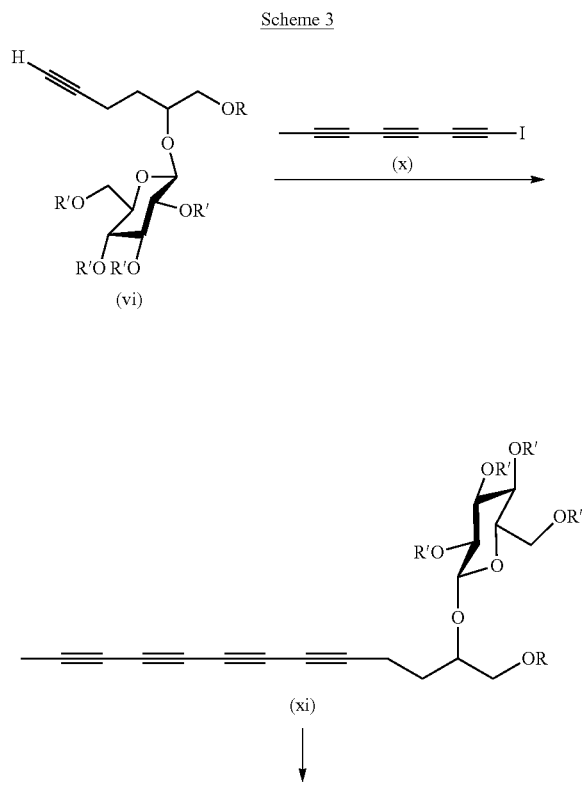

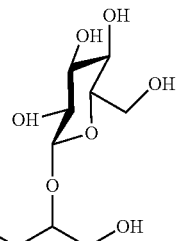

Scheme 3 demonstrates a coupling reaction between an acetylene derivative (vi), obtained from Scheme 1, and 1-iodohepta-1,3,5-triyne (x), obtained from Scheme 2, to a tetrayne compound (xi). Removal of protecting groups affords a polyacetylenic compound, 2β-D-glucopyranosyloxy-1-hydroxytrideca-5,7,9,11-tetrayne, a compound of this invention.

Synthetic chemistry transformations useful in synthesizing applicable compounds are described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999). L. Fieser and M. Fieser, Fieser and *Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A composition for oral administration can be any orally acceptable dosage form including capsules, tablets, emulsions, and aqueous suspensions, dispersions, and solutions. In the case of tablets, commonly used carriers include lactose and con starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

*Bidens pilosa* plants were collected. Approximately 10 kg of cleaned and crushed plants, in their entirety, was refluxed in 40 L of water for two hours. After removal of aqueous phase, insoluble materials was again refluxed in 25 L of water for two hours. The combined aqueous solutions (approximately 65 L) were evaporated in vacuo to yield a residue, which was subsequently suspended in 1.0 L of water and extracted with 1.0 L of n-butanol for three times. The n-butanol fraction was first evaporated on a vacuum rotary evaporator under reduced pressure and then lyophilized to provide a crude product of cytopiloyne (37.7 g).

The crude product was subsequently chromatographed over a RP-18 silica gel column with a $CH_3OH/H_2O$ gradient solvent system to give sub-fractions BPB1, BPB2, BPB3, and BPB4. The BPB3 fraction, eluted by 70% $CH_3OH$, was further fractionated by semi-preparative HPLC using a $CH_3OH/H_2O$ solvent system. Cytopiloyne was obtained and characterized by $^1$H NMR and $^{13}$C NMR.

$^1$H NMR (500 MHz, $CDOD_3$) δ 1.78 (2H, q, J=6.8 Hz), 1.98 (3H, s), 2.58 (2H, t, J=6.8 Hz), 3.19 (1H, dd, J=9.1, 7.8 Hz), 3.30 (1H, m), 3.34 (1H, m), 3.59 (2H, m), 3.65 (1H, dd, J=12.0, 6.5 Hz), 3.75 (1H, p, J=6.8 Hz), 3.85 (1H, dd, J=12.0, 1.7 Hz), 4.32 (1H, d, J=7.8 Hz); $^{13}$C NMR (125 MHz, $CDOD_3$) δ 3.8, 16.1, 31.4, 60.0, 60.9, 61.8, 62.4, 62.6, 64.9, 65.8, 66.2, 71.5, 75.2, 77.9, 81.6, 104.8.

Calculation of the percentage of *Bidens pilosa* powder (BPP) is as follows: *Bidens pilosa* powder weight/*Bidens pilosa* powder weight+basic chicken feed=% of BPP.

By 0.0005% to 15% (w/w) it meant that all ten-thousandth, thousandth, hundredth, tenth and integer unit amounts within the range are specifically disclosed as part of the invention. Thus, 0.0005%, 0.0006%0.0007% . . . 0.0.001%, 0.002%, 0.003% . . . 0.01%, 0.02%, 0.03% . . . 0.1%, 0.2%, 0.3%, 0.4%, 0.5%, 0.6%, 0.7%, 0.8%, 0.9% and 1%, 2%, 3%, 4% . . . 13%, 14%, and 15% unit amounts are included as embodiments of this invention.

By 0.05% to IS % (w/w) it meant that all hundredth, tenth and integer unit amounts within the range are specifically disclosed as part of the invention. Thus, 0.05%, 0.06%, 0.07% . . . 0.01%, 0.02%, 0.03% . . . 0.0.1%0.2%0.3% . . . and 1%, 2%, 3%, 4% . . . 13%, 14%, and 15% unit amounts are included as embodiments of this invention. By 0.1% to 15% (w/w) it meant that all tenth and integer unit amounts within the range are specifically disclosed as part of the invention. Thus, 0.1%, 0.2%, 0.3% . . . and 1%, 2%, 3%4% . . . 13%, 14%, and 15% unit amounts are included as embodiments of this invention. By 1% to 15% (w/w) it meant that all integer unit amounts within the range are specifically disclosed as part of the invention. Thus, 1%, 2%, 3%, 4% . . . 13%, 14%, and 15% unit amounts are included as embodiments of this invention. By 1% to 10% (w/w) it meant that all integer unit amounts within the range are specifically disclosed as part of the invention. Thus, 1%, 2%, 3%, 4% . . . 8%, 9%, and 10% unit amounts are included as embodiments of this invention. By 1 to 5% (w/v) it meant that all integer unit amounts within the range are specifically disclosed as part of the invention. Thus, 1%, 1-2%, 1-3%, 1-4%, 2%, 2-3%, 2-4%, 2-5%, 3%, 3-4%, 3-5%, 4%, 4-5% and 5% unit amounts are included as embodiments of this invention.

Examples

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Animals, all animal-related protocols in this study were in accordance with the guidance for the Use of Laboratory Animals.

Newborn crossbred pigs (Duroc×Landrace×Yorkshire) were reared in slatted metal floor farrowing crates with sows with extra heat provided. Pigs were teeth clicked, tail docked and iron injected, and males castrated. No creep feed was provided. After weaning at 24 days, 50 pigs with nearest body weight (7.42±0.38 kg) were selected, moved to nursery rooms and assigned, by body weight, to five groups. Each pen was 3.7×2.6 m in size with slatted metal floor and contained three nipple waters and two self-feeders, and extra heat was provided by infrared heating lamps.

Pigs were fed diets based on corn, full-fat soybean meal and whey powder supplemented with AGP or three different doses (high, middle and high doses) of *B. pilosa* for 4 weeks (FIG. 1). Nutrients of diets were provided to meet or exceed requirements for weanling pigs. Feed and water were fed ad libitum. Feed was provided in meal form.

Pigs were weighed and feed intake measured on a pen basis at the beginning and days 7, 14, 21 and 28 of the experiment. Pigs aged 28 days were challenged by natural infection, in which they were infected with pathogens present in pig pens, or by *Brachyspira* spp. The weight gain, teed intake and gain-to-feed ratio of pigs on a pen basis in each period were calculated. Feces score was monitored three times at 08.00, 12.00 and 16.00 hours daily using a subjective scoring system. Feces were scored per pen as follows: 1, severe diarrhea; 2, mid diarrhea; 3, soft feces; 4, normal feces; 5 firm but dry feces (Song, Y. S., V. G. Pérez, J. E. Pettigrew, C. Martinez-Villaluenga, and E. G. de Mejia. 2010 "Fermentation of soybean meal and its inclusion in diets for newly weaned pigs reduced diarrhea and measures of immunoreactivity in the plasma" Anim. Feed Sci. Technol. 159:41-49). To evaluate gut pathology, the intestines removed from each treatment group of sacrificed piglets were fixed with formalin and embedded with paraffin. The gut slides were stained with hematoxylin and eosin (H&E) and examined under a microscope.

The gut bacterial DNA collected from the feces of the pigs in *B. pilosa*-treated or non-treated groups were purified and used as templates for PCR amplification with 16S rRNA primers: forward primer 5'-TCGTCGGCAGCGTCA-GATGTGTATAAGA GACAGCCTACGGG-NGGCWGCAG (SEQ ID NO: 1), and reverse primer 5'-GTCTCGTGGGCTCGGAGA TGTGTATAAGA-GACAGGACTACHVGGGTATCTAATCC (SEQ ID NO: 2) to prepare 16S rRNA amplicons library. The 16S rRNA amplicons for the illumine MiSeq system was used for taxonomy and classification of gut microbiota in weaning pigs. In order to prepare 16S rRNA amplicons library, the primer pair sequences for the V3 and V4 region that create a single amplicon of approximately 460 bp. Amplify the V3 and V4 region and using a limited cycle PCR, add Illumina sequencing adapters and dual-index barcodes to the amplicon target. Using the full complement of Nextera XT indices, up to 96 libraries can be pooled together for sequencing. Sequence on MiSeq—Using paired 300-bp reads, and MiSeq V3 reagents, the ends of each read are overlapped to generate high-quality, full-length reads of the V3 and V4 region in a single 65-hour run. The results of 16S rRNA gene amplicons sequencing will be analyzed by MiSeq Reporter, BaseSpace and Greengenes database to do taxonomy and classification of gut microbiota.

Statistical Analysis

Data were analyzed using STATRAPHIC plus software by Statistical Graphics Corp. Values are presented as means±standard deviation (s.d.). ANOVA analysis and/or Student's t-test were used to evaluate the differences between control (0% BP) and treatment groups. A significance level of 5% was adopted for the analysis.

Results

Effect of *B. pilosa* on diarrhea associated with gut pathology in weaning pigs. Weaning piglets were grouped and fed with antibiotic growth promoter (AGP), standard diet (0% BP, CTL) and standard diet containing *B. pilosa* powder (LBP (1%), MBP (2%) and HBP (5%)) for 4 weeks (FIG. 1). Pigs were infected with pathogens inside pig pens (natural infection) or *Brachyspira* spp. on day 28. The feces score of these pigs was monitored three times a day and recorded diarrhea condition. Hundred percent of weaning pigs fed with standard diet group (0% BP) had lower scores and developed diarrhea in the first week (FIG. 2). However, diet containing AGP or *B. pilosa* could reduce diarrhea occurrences in the weaning pigs by 75% to 95% (FIG. 2). *B. pilosa* significantly decreased diarrhea (FIG. 2) and increased feces score (Table 1) in weaning pigs as evidenced by the pig groups fed with high and middle doses. The effect on gut pathology in 5 groups of pigs was examined. The villi and crypts in the duodenum, jejunum and ileum in control pigs fed with standard diet (0% BP) were worse than those in the duodenum, jejunum and ileum in pigs fed with the diet containing different doses of *B. pilosa* as well as AGP (FIG. 3A). The villus-to-crypt length ratio of duodenum, jejunum and ileum in the control pigs (0% BP) was lower than that of duodenum, jejunum and ileum in the pigs fed with different doses of *B. pilosa* as well as AGP (FIG. 3B). The data suggest that *B. pilosa* inhibits diarrhea and gut pathology in pigs. Table 1 shows the effect of *B. pilosa* on improving feces score of weaning piglets.

TABLE 1

| Feces score[1,2] | AGP | CTL | LBP | MBP | HBP |
| --- | --- | --- | --- | --- | --- |
| Day 1 to 7 (1st wk) | 2.2 ± 0.1* | 1.2 ± 0.2 | 2.6 ± 0.4* | 2.1 ± 0.2* | 2.3 ± 0.3* |
| Day 8 to 14 (2nd wk) | 3.5 ± 0.4* | 2.1 ± 0.3 | 2.9 ± 0.3* | 3.4 ± 0.4* | 3.3 ± 0.6* |
| Day 15 to 21 (3rd wk) | 3.8 ± 0.3* | 2.2 ± 0.6 | 3.8 ± 0.5* | 3.9 ± 0.3* | 3.5 ± 0.7* |
| Day 22 to 28 (4th wk) | 3.7 ± 0.7* | 2.6 ± 0.4 | 3.5 ± 0.7* | 3.6 ± 0.7* | 3.9 ± 0.4* |

[1]Mean ± S.D. (number of swine in each treatment group is 10) ANOVA was used to compare the difference between control (0% BP) and each treatment group in the 1st to 4th weeks and $p < 0.05$ (*) are shown.
[2]Feces were scored per pen as follows: 1, severe diarrhea; 2, mild diarrhea; 3, soft feces; 4, normal feces; 5 firm but dry feces.

Figure 4:
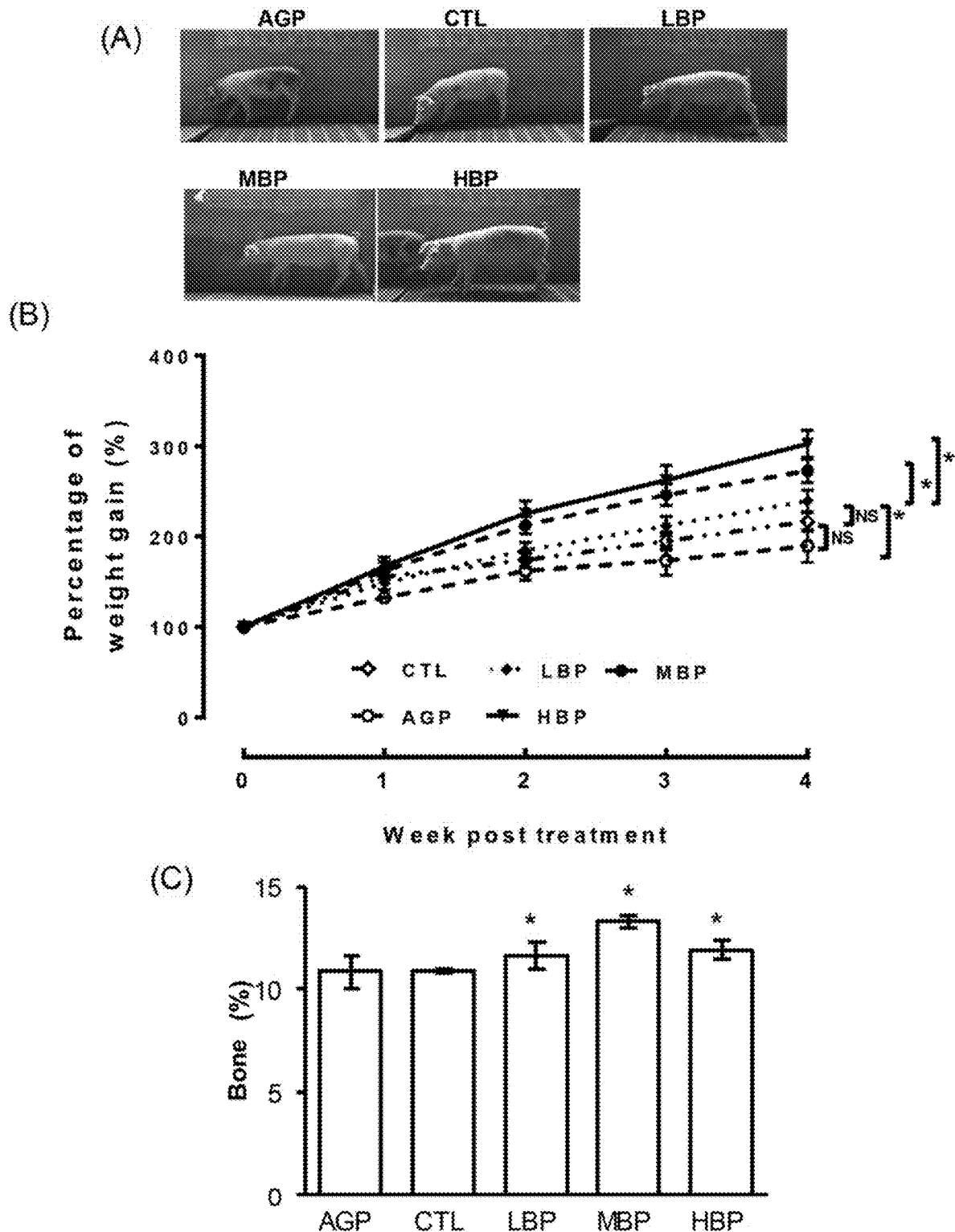
FIG. 4 shows the effects of *B. pilosa* on body length (4A), percentage of body weight (4B) and percentage of bone weight in weaning piglets (4C). Five groups of 4-week-treated weaning piglets fed with standard diet (0% BP) and standard diet containing *B. pilosa* powder (BP) and AGP for 4 weeks. Body size (4A), body weight (4B), and bone weight (4C) were monitored weekly for 4 weeks. The number of piglets per group was 10. ANOVA was used to compare the difference between control (0% BP) and each treatment in the end of $4^{th}$ treatment weeks.

*B. pilosa* improves percentage of weight gain, carcass weight, bone weight and lowers FCR. The benefits of *B. pilosa* for growth performance in pigs were evaluated. We first monitored the body weight gain and feed conversion rate (FCR) of pigs fed with a standard diet or containing different doses of *B. pilosa*. It was found that pigs fed with *B. pilosa* had better body size (FIG. 4A), weight gain (FIG. 4B), carcass weight (Table 2), carcass length (Table 2), and bone weight (FIG. 4C) than those fed with a standard diet or AGP groups. Consistently, *B. pilosa* significantly decreased FCR in pigs in *B. pilosa*-treated groups in a dose dependent manner (Table 3). The data collectively demonstrated that *B. pilosa* promoted total weight, carcass, and bone but diminished FCR. Table 2 shows the improvement of *B. pilosa* on carcass quality of weaned pigs. Table 3 shows the effect of *B. pilosa* on reduced feed conversion rate in weaned piglets.

TABLE 2

| Pig[a] | AGP | CTL | LBP | MBP | HBP |
| --- | --- | --- | --- | --- | --- |
| Carcass weight (kg) | 12.39 ± 0.24[b] | 11.01 ± 0.64 | 13.07 ± 0.39[c] | 13.99 ± 0.57[c] | 14.67 ± 0.53[c] |
| Carcass length (cm) | 40.17 ± 0.95 | 39.82 ± 1.04 | 41.75 ± 0.53 | 42.50 ± 0.35 | 42.17 ± 0.38 |

[a]Five groups of 4-week-old weaning piglets fed with standard diet (CTL) and standard diet containing low, medium and high doses of *B. pilosa* powder (LBP, MBP and HBP) and AGP (antimicrobial growth promoter) for 4 weeks.
[b]The data are expressed as Mean ± SEM, and the pig number was 3 for each group. The difference between control group and AGP group is statistically significant ($p < 0.05$).
[c]The difference between control group and *B. pilosa* group is statistically significant ($p < 0.05$).

TABLE 3

| | AGP | CTL | LBP | MBP | HBP |
| --- | --- | --- | --- | --- | --- |
| Body weight of initiate (Age of day 35) | 7.99 ± 1.34 | 7.16 ± 0.96 | 7.64 ± 1.15 | 7.06 ± 1.51 | 7.27 ± 1.51 |
| Body weight of end (Age of day 64) | 16.93 ± 1.57 | 13.24 ± 3.25 | 17.97 ± 1.45 | 18.79 ± 1.73 | 21.49 ± 2.92 |
| Increase of body weight (kg) | 8.94 ± 1.43 | 6.07 ± 3.74 | 10.33 ± 1.63 | 11.73 ± 1.41 | 14.22 ± 2.31 |
| Total feed intake (kg) | 15.72 ± 1.60 | 10.95 ± 1.13 | 16.01 ± 1.14 | 17.88 ± 1.73 | 21.82 ± 4.10 |
| Feed conversion ratio (FCR) | 1.75 | 1.80 | 1.55* | 1.52* | 1.53* |

Mean ± S.D. (number of swine in each treatment group is 10) ANOVA was used to compare the difference between control (0% BP) and each treatment and $p < 0.05$ (*) are shown.

Figure 5:
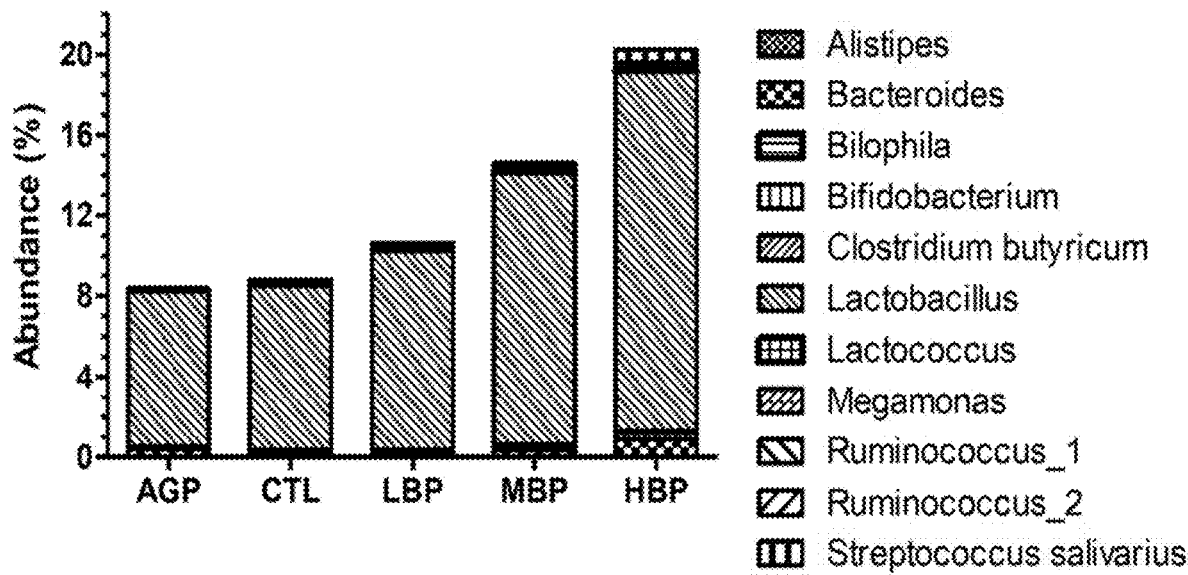
FIG. 5 shows the effect of *B. pilosa* on the percentage change in intestinal microbiota (probiotics) in the weaned stage piglets.
Figure 6:
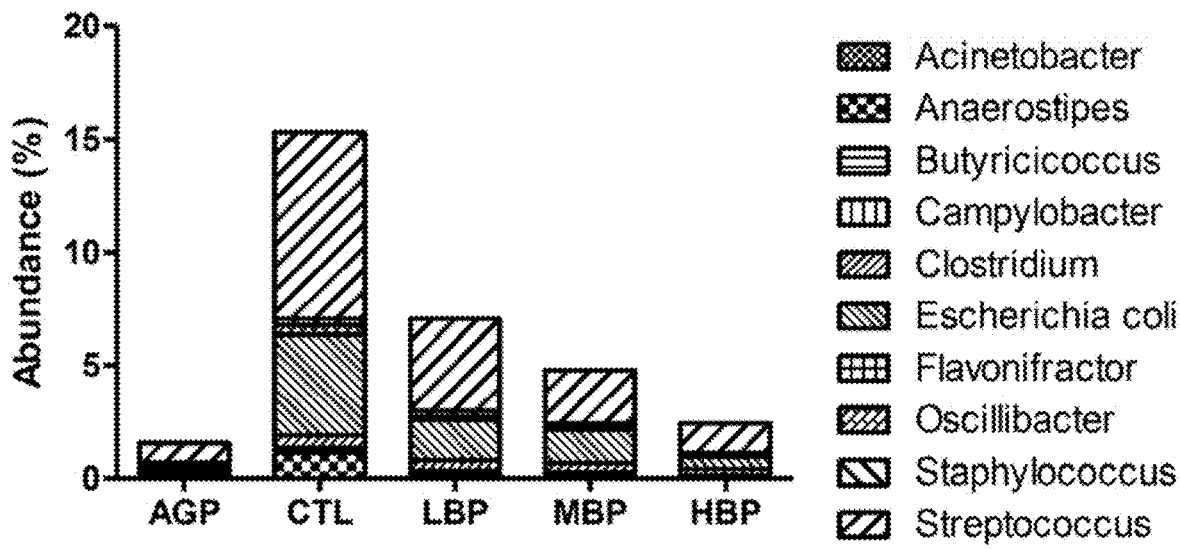
FIG. 6 shows the effect of *B. pilosa* on the percentage change in intestinal microbiota (pathogens) in the weaned stage piglets.

Overview of weaning pig gut microbiota in *B. pilosa*-treated or non-treated groups. We analyzed the effect of *B. pilosa* on gut bacteria in each group of pigs. Next-generation sequencing analysis of 16S rRNA amplicons of gut bacteria was conducted to uncover the bacterial communities in the guts of weaning pigs aged 56 days. The subset of bacterial genera, *Bacteroides, Megamonas,* Lachruspiraceae, *Lactobacillus* and Rumirococcaceae was increased in *B. pilosa*-fed pigs (FIG. 5). All the above genera were reported to be beneficial microbiota. It was also found in pig gut bacterial genera associated with gut pathology were decreased (FIG. 6). These bacteria, including *Butyricicoccus, Anaeroplasma, Anaerostipes, Phascolarctobacterium, Clostridium* (Ruminococcaceae), *Enterococcus, Acinetobacter, Campylobacteria, Escherichia/Shigella* and *Clostridium* (Clostridiaceae), are known as opportunistic pathogens of zoonotic origin, which not only affect the domestic animal industry but also cause public health problems in humans.

Figure 7:
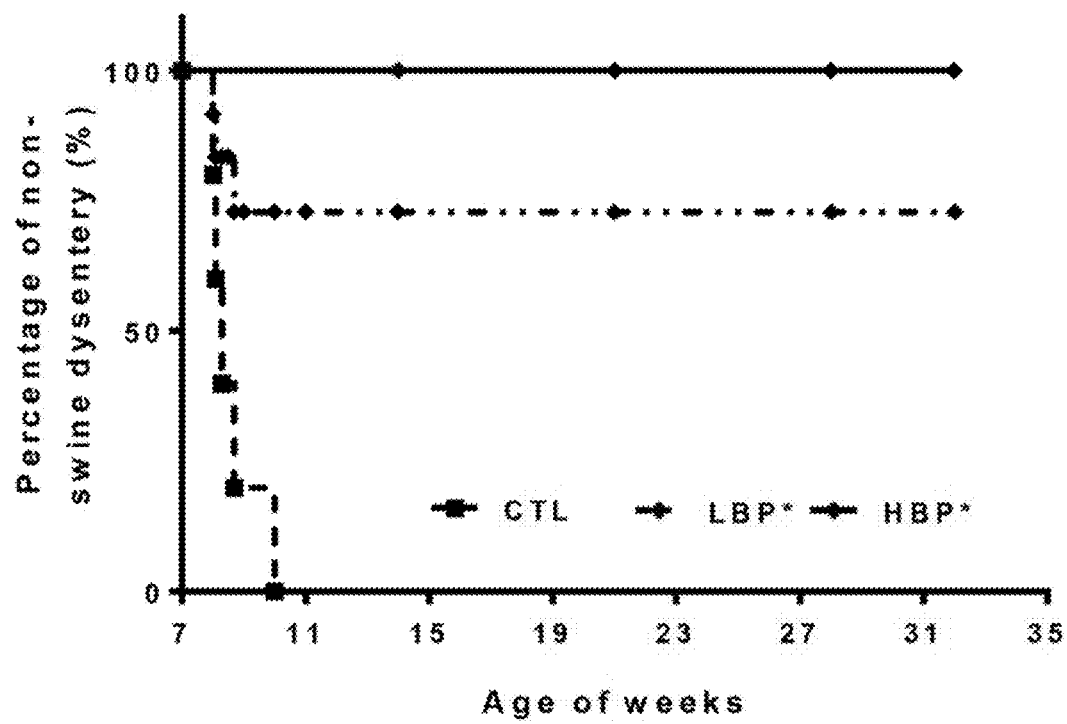
FIG. 7 shows the effect of *B. pilosa* on swine dysentery in the growing/finishing stage pigs. Pigs developed swine dysentery after *Brachyspira* spp. challenge. Occurrence of swine dysentery was monitored every day after weaning stage until age of 35 weeks. The pig number was 10 for each group. The p values were estimated by Kaplan-Meier log-rank test to determine the difference in outcomes between control (0% BP) and each treatment groups and p<0.05 (*) are shown (A). Table showing the p-values for pairwise comparisons of non-swine dysentery curves (B).

Effect of *B. pilosa* on swine dysentery in the growing/finishing stage pigs. We monitored clinical behavior of pigs in growing/finishing stage after weaning stage until age of 35 weeks. All pigs were challenged with *Brachyspira* spp. Control pigs fed with standard diet group (0% BP, CTL, FIG. 7A) developed swine dysentery in the first month after weaning stage. The pigs fed with low dose (LBP, FIG. 7A) and high dose (HBP, FIG. 7A) of *B. pilosa* reduced swine dysentery by 75% and 100%, respectively (FIG. 7A). Statistical analysis of these experiments were performed and shown in FIG. 7B.

Effect of *B. pilosa* on reduction of the presence of viruses and bacteria in pigs. We also examined the effect of *B. pilosa* on the number of pigs with the presence of viruses, and pathogenic bacteria after natural infection in pig farms. Seven out of 7 control pigs, fed with standard diets, were infected with porcine epidemic diarrhea virus (PEDV) (CTL, PEDV, Table 4). In contrast, *B. pilosa* dose-dependently reduced the presence of PEDV in pigs fed with the diet containing different doses of *B. pilosa* (LBP, MBP, and HBP, PEDV, Table 4). It was the case for transmissible gastroenteritis coronavirus (TGEV, Table 4) and rotavirus (RV, Table 4). Similarly, 7 out of 7 control pigs, fed with standard diets, were positive for *C. perfringens* (CTL, *Clostridium perfringens*, Table 4). In contrast, *B. pilosa* dose-dependently reduced the presence of *C. perfringens* in pigs fed with the diet containing different doses of *B. pilosa* (LBP, MBP, and HBP, *Clostridium perfringens*, Table 4). It was also the case for enteropathogenic *E. coli* and *Salmonella* spp. (*E. coli* and *Salmonella* spp., Table 4). Unfortunately, *B. hyodysenteriae* was not detectable (*Brachyspira hyodysenteriae*, Table 4).

Overall, *B. pilosa* reduced not only the clinical symptoms of diarrhea/dysentery, but also proportion of diarrheagenic pathogens in the guts of the pigs, suggesting this plant not only inhibited the pathogenic bacteria and viruses in the diarrhea conditions in weaning stage, but also reduce swine dysentery in growing/finishing stage.

Table 4 shows the number of pigs which seven pathogens in their saliva, blood and colonic samples were detection by multiplex PCR DNA biochip or ELISA in the end-day weaning stage. The term "ND" stands for "non-detectable".

TABLE 4

| Pathogens | AGP diet (# positive/# tested)[a] | CTL | LBP | MBP | HBP |
|---|---|---|---|---|---|
| PEDV (coronavirus) | 4/7 | 7/7 | 3/7 | 2/7 | 1/7 |
| TGEV (coronavirus) | 4/7 | 4/7 | 1/7 | 1/7 | ND |
| Rotavirus (RV) | 2/7 | 3/7 | 1/7 | 1/7 | ND |
| *Brachyspira hyodysenteriae* | ND | ND | ND | ND | ND |
| *Clostridium perfringens* | ND | 7/7 | ND | ND | ND |
| Enteropathogenic *E. coli* | 1/7 | 5/7 | ND | ND | ND |
| *Salmonella* spp. | ND | 1/7 | ND | ND | ND |

[a]Pig saliva, blood and colonic samples of 7 pigs from FIG. 2 were tested for the pathogens by multiplex PCR DNA biochip or ELISA in the end-day weaning stage. The results are presented by number of positive and tested samples. PEDV, TGEV, RV were detected by multiplex PCR-DNA biochip. *Brachyspira hyodysenteriae* was detected by PCR. *Clostridium perfringens*, *E. coli* and *Salmonella* spp. were detected by ELISA.

In summary, weaning swine were fed with a chow diet containing an antibiotic or *B. pilosa* as a feed additive for 28 days. Weight gain, food intake, feces score, serum biochemistry, gut pathology, modulation of gut microbiota, and carcass quality were analyzed. Animals treated with antibiotic or *B. pilosa* both showed reduction in diarrhea. However, 75% to 95% of piglets in the *B. pilosa*-treated group showed protection whereas only 75% of the antibiotic-treated group was protected. In addition, animals treated with *B. pilosa* had a better growth advantage and body shape score than the control and antibiotic groups. Besides, animals treated with *B. pilosa* had a lower rate of swine dysentery and viral infections than the control and antibiotic groups at different growth stages. In conclusion, *B. pilosa* reduces swine diarrhea and dysentery at different stages of pigs.

All references cited and discussed in this specification are incorporated herein by reference in their entireties and to the same extent as if each reference was individually incorporated by reference.

What is claimed is:

1. A method for treating, inhibiting and decreasing the occurrence of diarrhea associated with pathogenic gut microbiota selected from the group consisting of *Brachyspira*, porcine epidemic diarrhea virus (PEDV), transmissible gastroenteritis coronavirus (TGEV) and Rotavirus (RV), and increasing carcass weight and bone weight in a pig in need thereof, comprising:
administering to the pig in need thereof a composition consisting essentially of a therapeutically effective amount of *Bidens pilosa* extract and swine feed.

2. The method of claim 1, wherein the composition consists of the therapeutically effective amount of the *Bidens pilosa* extract and the swine feed.

3. A method for treating, inhibiting and decreasing the occurrence of diarrhea associated with pathogenic gut microbiota selected from the group consisting of *Brachyspira*, porcine epidemic diarrhea virus (PEDV), transmissible gastroenteritis coronavirus (TGEV) and Rotavirus (RV), and increasing carcass weight and bone weight in a pig in need thereof, comprising:
administering to the pig in need thereof a composition consisting essentially of a therapeutically effective amount of *Bidens pilosa* extract.

4. The method of claim 1, wherein the pig in need thereof is a weaning pig.

5. The method of claim 1, wherein the pig in need thereof is a growing and/or finishing stage pig.

6. The method of claim 1, wherein the *Bidens pilosa* extract comprises an active compound of formula (I):

$$R_1-(C\equiv C)_m-(\underset{H}{C}=\underset{H}{C})_n-()_o-()_p\begin{matrix}OR_2\\OR_3,\end{matrix}$$
(I)

wherein
$R_2$ is H or $CH_3$;
$R_2$ is monosaccharide;
$R_3$ is H or $COCH_2COOH$;
m=3 or 4;
n=0 or 1;
o=1 or 2; and
p=1 or 2.

7. The method of claim 1, wherein the *Bidens pilosa* extract is in a powder form.

8. The method of claim 1, wherein the composition is in the form of food, or a medicine.

9. The method of claim 1, wherein the *Bidens pilosa* extract is at a dosage of no less than 1 μg/kg body weight of the animal in need thereof.

10. The method of claim 1, wherein the *Bidens pilosa* extract ranges from 1% to 5% (w/w).

11. The method of claim 2, wherein the *Bidens pilosa* extract ranges from 1% to 5% (w/w).

12. The method of claim 1, wherein the *Bidens pilosa* extract comprises cytopiloyne.

13. The method of claim 3, wherein the pig in need thereof is a weaning pig.

14. The method of claim 2, wherein the *Bidens pilosa* extract comprises cytopiloyne.

15. The method of claim 3, wherein the composition is in the form of swine feed or a medicine.

16. The method of claim 3, wherein the *Bidens pilosa* extract is in a powder form.

17. The method of claim 1, wherein in the administering step, the pig is not infected by the pathogenic gut microbiota selected from the group consisting of *Brachyspira*, PEDV, TGEV and RV.

18. The method of claim 3, wherein in the administering step, the pig is not infected by the pathogenic gut microbiota selected from the group consisting of *Brachyspira*, PEDV, TGEV and RV.

19. The method of claim 1, wherein in the administering step, the pig is infected by at least one pathogenic gut microbiota selected from the group consisting of *Brachyspira*, PEDV, TGEV and RV.

20. The method of claim 3, wherein in the administering step, the pig is infected by at least one pathogenic gut microbiota selected from the group consisting of *Brachyspira*, PEDV, TGEV and RV.

* * * * *

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S rRNA forward primer
<220> FEATURE:
<221> NAME/KEY: misc_feature
<222> LOCATION: (42)..(42)
<223> OTHER INFORMATION: n is a, c, g, or t

<400> SEQUENCE: 1
```

```
tcgtcggcag cgtcagatgt gtataagaga cagcctacgg gnggcwgcag              50

<210> SEQ ID NO 2
<211> LENGTH: 55
<212> TYPE: DNA
<213> ORGANISM: Artificial Sequence
<220> FEATURE:
<223> OTHER INFORMATION: 16S rRNA reverse primer

<400> SEQUENCE: 2
gtctcgtggg ctcggagatg tgtataagag acaggactac hvgggtatct aatcc        55
```